United States Patent [19]

Boxus

[11] 3,972,146

[45] Aug. 3, 1976

[54] PROCESS FOR PROPAGATING STRAWBERRY PLANTS

[75] Inventor: Philippe Boxus, Brussels, Belgium

[73] Assignee: Station des Cultures Fruitieres et Maraicheres, Gembloux, Belgium

[22] Filed: July 17, 1975

[21] Appl. No.: 596,908

[30] Foreign Application Priority Data

July 19, 1974  Belgium .............................. 146738

[52] U.S. Cl. .................................................. 47/58
[51] Int. Cl.² ........................................... A01G 1/00
[58] Field of Search ......................................... 47/58

[56] References Cited
UNITED STATES PATENTS

| | | |
|---|---|---|
| 3,514,900 | 6/1970 | McDade ................................ 47/58 |
| 3,683,550 | 8/1972 | Corlett et al. ........................... 47/58 |
| 3,816,960 | 6/1974 | Gudin et al. ............................ 47/58 |
| 3,821,864 | 7/1974 | Stottlemyer ............................ 47/58 |

FOREIGN PATENTS OR APPLICATIONS 1,387,821   3/1975   United Kingdom..................... 47/58

*Primary Examiner*—Robert E. Bagwill
*Attorney, Agent, or Firm*—Kurt Kelman

[57] ABSTRACT

Strawberry plants are propagated by placing the normally dormant axillary or adventive shoots located on a strawberry plantlet at the base of a leaf stalk in an aqueous nutrient medium containing 0.01 to 100 mg/l N-benzyl-6-aminopurine until a multiplicity of shoots is formed, separating the formed shoots, and transplanting the separated shoots into another nutrient medium. The first medium must contain 0.01 to 100 mg/l N-benzyl-6-aminopurine, and the last transplanting medium should not contain more than 0.1 mg/l of the cytokinin in order to permit normal formation of leaves and roots.

4 Claims, No Drawings

PROCESS FOR PROPAGATING STRAWBERRY PLANTS

The present invention relates to the asexual propagation of plants, and particularly of strawberry plants.

It is known to propagate strawberries by runners and thereby to obtain thirty to fifty new plants from one mother plant in one year.

It has now been found possible to obtain millions of new plants per year from a single mother plant by bringing to life the normally dormant axillary or adventive shoots located at the base of the leaf stalks of a plantlet grown in a sterile manner by culturing the plantlet in a nutrient medium containing cytokinin.

When an axillary or adventive shoot is placed in a nutrient medium containing cytokinin, axillary or adventive shoots are propagated and this continues for as long as the cytokinin remains active, usually about six to eight weeks.

The new shoots thus obtained are separted and individualized and can then in turn propagate if they are transplanted into a medium enriched with cytokinin.

According to a feature of the invention, the propagation of the shoots is stopped when desired by eliminating the cytokinin. Thereafter, the shoots act as young strawberry plants forming leaves and roots which can be planted in soil where they function in the same way as natural runners.

In the laboratory, firstly a plantlet which had been raised in a sterile manner and obtained from meristems or by some other method was acquired to serve as the "starting material." It was aseptically transplanted into 25 × 150 mm test tubes containing 15 ml of a nutrient solution containing the macro-elements of a Knop mineral solution, the micro-elements of Murashige and Skoog, 0.5 mg/l of nicotinic acid, 0.5 mg/l of HCl pyridoxine, 2.0 mg/l of glycine, 0.1 mg/l of HCl thiamine, 100 mg/l of mesoinositol, 1.0 mg/l of indolyl butyric acid, 40.0 g/l of glucose and 8.0 g/l of agar. Prior to autoclaving, the pH of the medium was adjusted to 5.6. To this nutrient medium which proved satisfactory in all our tests, it is necessary to add a quantity of cytokinin in order to obtain a large-scale development of axillary or adventive shoots.

Our tests showed that 1 mg/l of N-benzyl-6-aminopurine was effective for all the varieties of strawberries tested. Below 0.01 mg/l and above 100 mg/l the doses are ineffective or toxic.

After preparation, the nutrient solutions were poured into tubes or jars and sterilized in an autoclave at 110° C for 15 minutes. Other temperatures and times may be chosen for such sterilization as is conventional.

After spending 3 – 4 weeks in the sterile nutrient medium, the plantlet started to shoot by development of axillary or adventive shoots. This propagation of adventive or axillary shoots continued for at least 3 – 4 weeks. By then, the plantlet had formed a mass of shoots (15 – 30 and sometimes more) which only developed a few leaves and roots. This mass of shoots was separated to individualize each shoot in the sterile medium, and the separated shoots were transplanted each into a fresh nutrient medium.

Our experiments have shown that in a cytokinin-rich medium containing 1 mg/l N-benzyl-6-aminopurine, shoot formation continues at a rate of at least 15 – 30 every 6 – 8 weeks.

Thus separation and transplanting can take place as often as desired at the time when the necessary quantity of shoots is available.

When the cytokinin is omitted from the medium or at least reduced to less than 0.1 mg/l of N-benzyl-6-aminopurine, the separated shoots develop leaves and roots after about 3 weeks.

After a further 1 or 2 weeks, the plantlets can be transplanted into a relatively light compost soil which is preferably not sterile in order to avoid surface mildew. The transplanted plantlets easily start growing again provided that a humid atmosphere is maintained (mist spray or relatively tightly sealed transparent plastic tanks). Three to five weeks later, the transplanted plantlets have the vigor and size of a normal runner.

The growing room used in connection with the aforedescribed accelerated propagation was held at a constant temperature of 24°C with artificial lighting (6 40W TL cubes per 120 m² of shelf) during 16 hours daily. The relative humidity of the air is unimportant. The temperature may be chosen between 10 and 30°C and either be kept constant or varied between night and day. Light can be supplied by any type of lamp provided that a minimum threshold intensity of 1,500 – 2,000 lux is maintained. It is also possible to work in a greenhouse, but a back-up lighting system is necessary if the shelves are superimposed in order to illuminate the lower shelves.

Culturing takes place in test tubes or in sterilizable jars. Jars having a capacity between one half and three quarters of a liter have proved particularly suitable for obtaining a large number of plants in a small volume of nutrient medium.

The passage from shoot formation to the differentiation into plantlets with leaves and roots, followed by a return to shoot formation, was performed numerous times without impairing the characteristics of the plant material. The accelerated propagation process strictly reproduces the different varieties.

Propagation under sterile conditions ensures that the material produced is 100% healthy.

The invention has been described solely relative to one example and obviously various modifications can be made thereto without passing beyond the scope of the invention.

What is claimed is:

1. Process for the propagation of strawberry plants which comprises:
   a. placing a strawberry plantlet having a leaf stalk and normally dormant axillary or adventive shoots at the base of said leaf stalk in an aqueous nutrient medium capable of sustaining said plantlet until a multiplicity of shoots is formed, said medium containing an amount of a cytokinin sufficient to enhance the formation of said shoots;
   b. separating the formed shoots; and
   c. transplanting the separated shoots into another aqueous nutrient medium containing less than said amount of said cytokinin until each separated shoot develops leaves and roots, wherein said cyntokinin is N-benzyl6-aminopurine, said sufficient amount being 0.01 to 100 mg/l of said N-benzyl-6-aminopurine.

2. Process according to claim 1, wherein said separated shoots prior to said transplanting into said other nutrient medium are transplanted to an intermediate nutrient medium capable of sustaining the formed shoots, said intermediate medium containing 0.01 to 100 mg/l of said N-benzyl-6-aminopurine.

3. Process according to claim 1, wherein said sufficient amount is approximately 1 mg/l.

4. Process according to claim 1, wherein said other aqueous medium does not contain more than 0.1 mg/l of said N-benzyl-6-aminopurine.

* * * * *